United States Patent
Wang et al.

(10) Patent No.: US 10,548,933 B2
(45) Date of Patent: Feb. 4, 2020

(54) METHOD FOR PREPARING BROCCOLI PROTEIN PEPTIDE MIXTURE

(71) Applicants: ZHEJIANG HISUN PHARMACEUTICAL CO., LTD., Taizhou, Zhejiang (CN); ZHEJIANG TELEY BIOTECHNOLOGY CO., LTD., Linhai, Zhejiang (CN)

(72) Inventors: Jidong Wang, Zhejiang (CN); Huan Qi, Zhejiang (CN); Xiaohe Zheng, Zhejiang (CN); Hui Zhang, Zhejiang (CN); Yongdong Wang, Zhejiang (CN); Hailing Tang, Zhejiang (CN); Haiming Lin, Zhejiang (CN)

(73) Assignees: ZHEJIANG HISUN PHARMACEUTICAL CO., LTD., Taizhou, Zhejiang (CN); ZHEJIANG TELEY BIOTECHNOLOGY CO., LTD., Linhai, Zhejiang (CN)

( * ) Notice: Subject to any disclaimer, the term of this patent is extended or adjusted under 35 U.S.C. 154(b) by 71 days.

(21) Appl. No.: 15/571,625

(22) PCT Filed: May 3, 2016

(86) PCT No.: PCT/CN2016/080880
§ 371 (c)(1),
(2) Date: Nov. 3, 2017

(87) PCT Pub. No.: WO2016/177309
PCT Pub. Date: Nov. 10, 2016

(65) Prior Publication Data
US 2018/0147248 A1 May 31, 2018
US 2019/0038694 A2 Feb. 7, 2019

(30) Foreign Application Priority Data
May 4, 2015 (CN) .......................... 2015 1 0216844

(51) Int. Cl.
*A61K 36/31* (2006.01)
*C12P 21/06* (2006.01)
*A23L 33/185* (2016.01)
*A61P 39/06* (2006.01)
*A61P 3/06* (2006.01)
*A61K 38/01* (2006.01)

(52) U.S. Cl.
CPC .......... *A61K 36/31* (2013.01); *A23L 33/185* (2016.08); *A61K 38/011* (2013.01); *A61P 3/06* (2018.01); *A61P 39/06* (2018.01); *C12P 21/06* (2013.01); *C12Y 304/00* (2013.01); *C12Y 304/21004* (2013.01); *C12Y 304/22002* (2013.01); *C12Y 304/22032* (2013.01); *C12Y 304/23* (2013.01); *C12Y 304/25001* (2013.01); *A23V 2002/00* (2013.01)

(58) Field of Classification Search
None
See application file for complete search history.

(56) References Cited

U.S. PATENT DOCUMENTS

2010/0136173 A1* 6/2010 Tang ................... C07K 14/415
426/63
2014/0323702 A1 10/2014 Dahms et al.

FOREIGN PATENT DOCUMENTS

| CN | 101294183 A | 10/2008 |
| CN | 101993480 A | 3/2011 |
| CN | 105524963 A * | 4/2016 |
| JP | 2000212198 A | 8/2000 |
| JP | 2004180578 A | 7/2004 |
| JP | 2014533705 * | 12/2014 |
| JP | 2014533705 A | 12/2014 |
| WO | 2010125910 | 11/2010 |

OTHER PUBLICATIONS

Tsai C. et al. Growth Inhibition and Antioxidative Status Induced by Selenium Enriched Broccoli Extract and Selenocompounds in DNA Mismatch Repair Deficient Human Colon Cancer Cells. Food Chemistry 139:267-273, 2013. (Year: 2013).*
International Search Report for International Application No. PCT/CN2016/080880, dated Aug. 8, 2016, 3 pages.
Kong, X. et al., Enzymatic Preparation of Peptides from Vegetable Proteins, China Oils and Fats, Dec. 2013, pp. 16-17, vol. 38, No. 1.
Li, Y., Control of Bitter taste of Protein Enzymatic Hydrolysate, Science and Technology of Food Industry, Dec. 1997, p. 3, No. 3.
Li, J. et al., Progress in Study of Functional Polypeptides, College of Food Science, Biotechnology and Environmental Engineering, Sep. 2004, pp. 415-419, vol. 25, No. 11.
Tsai, C. F. et al. (2012). Growth inhibition and antioxidative status induced by selenium-enriched broccoli extract and selenocompounds in DNA mismatch repair-deficient human colon cancer cells,Food Chemistry, 139(1-4):267-73.
Bulletin of Toita Women's College, 2008, vol. 51, pp. 23-32. Abstract only.
Notification of Reasons for Refusal for Japanese Patent Application No. 2018-507765, dated Oct. 9, 2018, 8 pages.
(Continued)

*Primary Examiner* — Ralph J Gitomer
(74) *Attorney, Agent, or Firm* — Armstrong Teasdale LLP

(57) ABSTRACT

Provided is a method for preparing a broccoli protein peptide. The method uses a broccoli protein as the raw material, and obtains a broccoli protein peptide powder through the steps of preprocessing, enzymatic hydrolysis, terminating enzymatic hydrolysis, separation, and drying and the like. Also provided is the use of the prepared broccoli protein peptide in resisting oxidation, reducing cholesterol and lowering blood lipids.

10 Claims, No Drawings

(56) References Cited

OTHER PUBLICATIONS

Digestive enzyme agent, Japanese Pharmacopoeia, Pancreatin, 2013, pp. 1-13.
Office Action issued Jun. 25, 2019 in Japanese Application No. 2018-507765, 4 pages.

* cited by examiner

METHOD FOR PREPARING BROCCOLI PROTEIN PEPTIDE MIXTURE

This application is a National Phase application of PCT Application No.: PCT/CN2016/080880, filed on May 3, 2016 and also claims the priority of Chinese Patent Application No.: 201510216844.4, filed on May 4, 2015, the teachings and content of which are hereby incorporated by reference.

TECHNICAL FIELD

The present invention relates to a broccoli protein peptide, specifically, it relates to the preparation method for broccoli protein peptide and use of the obtained broccoli protein peptide.

TECHNICAL BACKGROUND

Broccoli (*Brassica oleracea* var. *italia*) is a variant of cruciferous *Brassica* cabbage, which is originally from Italy. Broccoli is rich in bioactive substances and nutrients, which is known as the "vegetable crown". The nutritional ingredient of broccoli is not only high in content, but also very comprehensive, which mainly includes proteins, carbohydrates, fats, minerals, vitamin C and carotene and so on. According to the analysis, every 100 g fresh broccoli bulb, contains 3.5 g-4.5 g protein, which is 3 times of that in cauliflower, 4 times of that in tomato. Patent ZL200910091131.4 discloses a broccoli leaf protein and its preparation method, wherein, a flocculated protein is obtained by flocculating broccoli juice by adding acid with heating or adding acid and flocculant, then broccoli leaf protein is obtained by drying the flocculated protein.

With the deepening of the research on nutrition and so on, the biological function of protein peptide has been paid more and more attention. Protein peptide is a kind of compound whose molecular structure is between amino acid and protein. It is the structure and function fragment of protein, and has dual function of regulating the physiological function of the body and providing nutrition for the body. Protein peptide has a variety of biological activities, such as: immune regulation, anti-thrombosis, antihypertensive, cholesterol-lowering, inhibition of bacteria and viruses, anticancer effect, anti-oxidation and scavenging free radicals, improving element absorption and mineral transportation, promoting growth and so on. Modern nutrition research found that the protein absorbed by human body are mainly digested and absorbed in the form of oligopeptide after the proteins have been hydrolyzed by the enzyme in the digestive tract, the proportion of the proteins absorbed in the form of free amino acid is very small (Li Jianrong, Feng Ping. Progress in Study of Functional Polypeptides. Food Science, 2004, 25 (11): 415-419), so the polypeptide can be absorbed and used by the body more easily and faster than the protein and free amino acids, and the protein is absorbed in the form of a polypeptide, and it is also beneficial to maximize the use of its biological active function. Mature protein peptide products in foreign markets are corn protein peptide breakfast drinks from Japan, milk protein peptides anti-alcohol drinks from South Korea. In the market of China, the products are soybean protein peptide immunoregulation health care products, milk protein peptide nutritional supplements and so on.

In view of the high protein content of broccoli, the production of broccoli protein peptide using broccoli as a raw material can provide a new way for the high value-added utilization of broccoli. The invention selects different enzymes to hydrolyze broccoli protein, and screens out the broccoli protein peptide powder with high specificity, the powder has anti-oxidation and cholesterol-lowering and lipid-lowering activities; and can be used to develop health food with related functions. In addition, the broccoli protein peptide that we developed can also be developed as protein supplements or can also be used as raw materials for the production of cosmetics, food additives, beverages and so on.

SUMMARY OF THE INVENTION

One object of the present invention is to provide a method for preparing a broccoli protein peptide and use thereof.

In one aspect, the present invention provides a method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: neutral protease (200-600 units per gram of raw material) is added to the pulp obtained in step (a), the temperature of the solution is controlled at 50±1° C., then the pH of the resulting solution is adjusted to 6.0-7.0 with NaOH, the time of enzymolysis is 3-4 hours;

(c) terminating the enzymolysis: the enzymolysis solution obtained in step (b) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, metal ions can be well complexed by adding EDTA, thereby reducing the impact of the metal ions on the protease activity in the subsequent steps.

The broccoli protein peptide prepared by this method has a good antioxidant effect, and its DPPH free radical scavenging rate can reach 10% of that of the reduced glutathione (about the reducing power of 10 mass % of GSH). In addition, the obtained broccoli protein peptide prepared according to the method also significantly reduces total cholesterol in a living organism and therefore can be used in the fields of food, medicine, health care products, or cosmetics and so on.

In another aspect, the present invention also provides another method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: papain (1000-3000 units per gram of raw material) is added to the pulp obtained in step (a), the temperature of the solution is controlled at 50±1° C., then the pH of the resulting solution is adjusted to 6.5-7.0 with NaOH, the time of enzymolysis is 3-4 hours;

(c) terminating the enzymolysis: the enzymolysis solution obtained in step (h) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, metal ions can be well complexed by adding EDTA, thereby reducing the impact of the metal ions on the protease activity in the subsequent steps.

The broccoli protein peptide prepared by this method has a good cholesterol lowering effect and a good blood lipid lowering effect, therefore can be used in the fields of food, medicine, health care products and so on.

In a third aspect, the present invention further provides a method for the preparation of a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(h) proteolysis: alkaline protease (200-600 units per gram of raw material) is added to the pulp obtained in step (a), the temperature of the solution is controlled at 50±1° C., then the pH of the resulting solution is adjusted to 9.0-9.5 with NaOH, the time of enzymolysis is 3-4 hours;

(c) terminating the enzymolysis: the enzymolysis solution obtained in step (b) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, metal ions can be well complexed by adding EDTA, thereby reducing the impact of the metal ions on the protease activity in the subsequent steps.

In a fourth aspect, the present invention further provides a method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: trypsin (5-15 units per grain of raw material) is added to the pulp obtained in step (a), the temperature of the solution is controlled at 50±1° C., then the pH of the resulting solution is adjusted to 8.0-8.5 with NaOH, the time of enzymolysis is 3-4 hours;

(c) terminating the enzymolysis: the enzymolysis solution obtained in step (h) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, metal ions can be well complexed by adding EDTA, thereby reducing the impact of the metal ions on the protease activity in the subsequent steps.

In a fifth aspect, the present invention further provides a method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: pepsin (5-15 units per gram of raw material) is added to the pulp obtained in step (a), the temperature of the solution is controlled at 36-38° C., then the pH of the resulting solution is adjusted to 1.5-2.5 with NaOH, the time of enzymolysis is 3-4 hours;

(c) terminating the enzymolysis: the enzymolysis solution obtained in step (h) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, complex metal ions can be well complexed by adding EDTA, thereby reducing the effect of the metal ions on the protease activity in the subsequent steps.

In a sixth aspect, the present invention further provides a method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: bromelain (1000-5000 units per gram of raw material) is added to the pulp obtained in step (a), the temperature of the solution is controlled at 40±1° C., then the pH of the resulting solution is adjusted to 6.0-7.0 with NaOH, the time of enzymolysis is 3-4 hours;

(c) terminating the enzymolysis: the enzymolysis solution obtained in step (b) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step (e) or (f) is concentrated and/or dried to obtain a broccoli protein peptide.

Wherein, anhydrous sodium sulfate is added in the step (a) in order to break the disulfide bond in the protein, complex metal ions can be well complexed by adding EDTA, thereby reducing the impact of the metal ions on the protease activity in the subsequent steps.

In a seventh aspect, the present invention further provides a method for preparing a broccoli protein peptide, comprising:

(a) protein preprocessing: water that is 4-8 times of weight of broccoli protein is added to the raw material broccoli protein to form a protein pulp, and anhydrous sodium sulfite with the mass-volume ratio of 0.05-0.1 g/l and EDTA with the mass-volume ratio of 0.02-0.05 g/l are further added to the protein pulp;

(b) proteolysis: compound protease (5-3600 units per gram of raw material) is added to the pulp obtained in step (a), the temperature of the solution is controlled at 50±1° C., then the pH of the solution is controlled at 8.0-8.5 within 0.5-1 hour, then the pH is no longer controlled, the time of enzymolysis is 3-4 hours;

(c) terminating the enzymolysis: the enzymolysis solution obtained in step (b) is heated to 80-90° C. for 5-15 minutes to inactivate the enzyme, the solution is cooled to room temperature;

(d) optionally, the liquid obtained in step (c) is centrifuged or filtered;

(e) the liquid obtained in step (c) or (d) is filtered with a membrane having a pore size of 100 to 500 nm;

(f) optionally, the filtrate obtained in step (e) is subjected to a debittering treatment with activated carbon or clay;

(g) the liquid obtained in step) is concentrated and/or dried to obtain a broccoli protein peptide.

Wherein, anhydrous sodium sulfate is added in the step (a) in order to break the disulfide bond in the protein, metal ions can be well complexed by adding EDTA, thereby reducing the effect of the metal ions on the protease activity in the subsequent steps.

Wherein the compound protease is selected from trypsin and neutral protease, or alkaline protease and papain, or alkaline protease and neutral protease.

The broccoli protein peptide prepared by this method (for example, using a compound protease of trypsin and neutral protease) has a good antioxidant effect, and its DPPH free radical scavenging rate can reach 10% of reduced glutathione (about the reducing power of 10 mass % of the GSH), therefore it can be used in the fields of food, medicine, health care products or cosmetics and so on.

In the method of the present invention, the "raw material", "broccoli protein" and "raw material broccoli protein" have the same meaning.

In an eighth aspect, the present invention provides a broccoli protein peptide prepared by the methods for preparing a broccoli protein peptide according to the present invention.

The broccoli protein peptide prepared by the method described in the present invention has the following advantages:

(1) The broccoli protein peptide prepared in the present invention has high purity, and the content of TCA (trichloroacetic acid) acid soluble protein of the broccoli protein peptide is more than 90%, the molecular weight distribution less than 10000 is above 90%, and the free amino acid represents 5-8%.

(2) The technical solution of the present invention is stable, the mass parameters such as the content of acid soluble protein, free amino acid and molecular weight distribution of the prepared broccoli protein peptide do not change significantly, thus suitable for industrial production.

The present invention will be further described by the following examples. It should be noted that these examples are provided for illustrating the present invention but not limiting.

EMBODIMENTS

In the following examples, the reagents and instruments used are those commonly used in the art, and can be purchased from a chemical or biological product/preparation company unless otherwise specified. The methods used in the following examples are conventional methods in the art. It will be apparent to those skilled in the art that the operation of these experiments and the corresponding results can be obtained without any doubt from the prior art or the operating manual provided by the manufacturer.

Example 1: Preparation of Raw Material Broccoli Protein (1) Raw material crushing: a whole broccoli (20 kg) was washed, dried, crushed with a crusher, and then pressed and filtered with a gauze (300 mesh) to obtain pressed juice, 9.5 L.

(2) Heating: the pressed juice from the last step was heated to 70° C. in a pot, the protein flocculates and floated on top, until there's no green at the bottom.

(3) Separating: the heated layered pressed juice was filtered to obtain a filter cake (flocculated protein) and a filtrate.

(4) Spray drying: 2.8 L of purified water was added to the flocculated protein obtained by filtration, mixed and homogenized, and then 682 g of raw material broccoli protein was obtained by spray drying (BUCHI, Small Spray Dryer B-290).

Example 2

(1) Protein Preprocessing: 100 g of broccoli protein prepared in example 1 was taken, and 500 ml of purified water, 0.05 g of anhydrous sodium sulfite and 0.02 g of EDTA were added and stirred to form a broccoli protein pulp.

(2) Proteolysis: 0.3 g of trypsin (4000 U/g) and 0.3 g of neutral protease (800,000 U/g) were added to the preprocessed broccoli protein pulp, stirred at 50° C. in a water bath, and the pH of the pulp was controlled at 8.2 with NaOH solution, the enzymolysis lasted for 3.5 h in total.

(3) Terminating of the enzymolysis and separation: the protein pulp that had been subjected to enzymolysis was heated to 80° C. for 5 minutes to inactivate the enzyme. After the pulp was cooled to room temperature, it was centrifuged at 10,000 rpm for 10 minutes with a high-speed centrifuge, then the supernatant was filtered through a 200 nm membrane to obtain about 400 ml of supernatant containing broccoli protein peptide. At this point, free nitrogen was used as a regular indicator, and the content of free nitrogen in the supernatant was measured as 1400 mg/l according to GB12143.2-1989.

(4) Debitterizing: 0.5% (W/V) of activated carbon was added to the obtained 400 ml supernatant, and the activated carbon was removed by filtering 30 minutes after debitterizing.

(5) Concentrating: the protein peptide solution was concentrated with a three-effect falling film evaporator until the solid content of the solution was greater than 10%.

(6) Spray Drying: the broccoli protein peptide supernatant obtained in step (4) was directly dried by spray drying (BUCHI, Small Spray Dryer B-290) to obtain 30 g of broccoli protein peptide.

The various indexes of the test and analysis of the obtained broccoli protein peptide are as shown in table 1. The test refers to the national standard prescribed test method for soybean protein peptide.

TABLE 1

Test and analysis results of broccoli protein peptide samples

| No. | Items of analysis | | Results of analysis |
|---|---|---|---|
| 1 | Free amino acid | | 6.39% |
| 2 | Molecular weight | Larger than 10000 D | 8.41% |
| 3 | distribution | Smaller than or equal to 10000 D | 91.59% |
| 4 | Urease | | Negative |

Example 3

(1) Sample Preprocessing: six broccoli protein samples prepared in example 1 were weighed, 10 g each, and were numbered A, B, C, D, E, F, 50 ml of distilled water was added respectively, the mixture were well shaken, then 5 mg of solid anhydrous sodium sulfite and 2 mg of solid EDTA were added.

(2) Proteolysis: proteases were added to the preprocessed six broccoli protein pulp samples according to the content of table 2, the pH value and temperature of the six samples were controlled according to table 2, Table 2

Formula for proteolysis

| | No. | | | | | |
|---|---|---|---|---|---|---|
| | A | B | C | D | E | F |
| Proteases | 0.03 g of 2709 alkaline protease (200,000 U/g) | 0.03 g of trypsin (4000 U/g) | 0.03 g of papain (800,000 U/g) | 0.03 g of 1389 neutral protease (200,000 U/g) | 0.05 g of pepsin (3000 U/g) | 0.1 g of bromelain (500,000 U/g) |
| pH value | 9.5 | 8.5 | 7.0 | 7.0 | 2.0 | 7.0 |
| Temperature | 50° C. | 50° C. | 50° C. | 50° C. | 37° C. | 40° C. |

The enzymolysis lasted for 3.5-4.0 h in total.

(3) Terminating of the enzymolysis and separation: the protein pulp A, D, C, D, E, F that had been subjected to enzymolysis were heated to 80° C. respectively for 5 minutes to inactivate the enzymes, after the temperature was decreased to room temperature, the pulps were filtered with filter clothes (400 mesh) and the supernatants were obtained. Then the filtered supernatants were filtered with a 200 nm membrane respectively to obtain supernatants containing broccoli protein peptide.

(4) The obtained broccoli protein peptide supernatants were lyophilized to obtain broccoli protein peptide samples digested with different enzymes.

Example 4

The antioxidant capacity was determined with the neutral protease and trypsin-digested peptide prepared in example 2, as well as the alkaline protease-digested peptide, the trypsin-digested peptide, the neutral protease-digested peptide, the papain-digested peptide and the pepsin-digested peptide prepared in example 3 used as samples, with soybean protein peptide and reduced glutathione used as controls (DPPH free radical scavenging rate method).

(1) DPPH (1,1-diphenyl-2-picrylhydrazyl) (25 mg) was weighed accurately, dissolved in absolute ethanol and the volume reached to 250 mL in a brown volumetric flask, DPPH solution with the concentration of 0.1 mg/mL was obtained and was kept in dark place to be supplied as standby.

(2) 1.0 mL sample solutions with different concentrations (100 mg/mL, 10 mg/mL, 1 mg/mL, 0.1 mg/mL) were taken, the solutions were placed in a 10 mL colorimetric tube respectively, 4.0 ml DPPH solution was added, the mixture was reacted at room temperature in a dark place for 30 minutes.

(3) The absorbance value was measured at 517 nm with the absolute ethanol as blank. The DPPH free radical scavenging rate was calculated according to the following formula.

$$\text{DPPH free radical scavenging rate } (\%) = A_0 - (A_s - A_c)/A_0 \times 100\%$$

In the formula. $A_0$—the absorbance value of 1.0 mL distilled water+3.0 mL solution $A_s$—the absorbance value of 1.0 mL sample solution+3.0 mL DPPH solution $A_c$—the absorbance value of 1.0 mL sample solution+3.0 mL absolute ethanol.

The experiment was repeated for three times, the average value of the scavenging rate was obtained (if the solution was turbid, the measurement was taken after centrifugation). The results are as shown in table 3.

TABLE 3

Results of the determination of the antioxidant effect of each protein peptide of broccoli

| Scavenging rate | concentration | | | |
|---|---|---|---|---|
| Peptide | 100 mg/ml | 10 mg/ml | 1 mg/ml | 0.1 mg/ml |
| Alkaline protease-digested peptide | 87.7% | 76.1% | 8.6% | 3.0% |
| Trypsin-digested peptide | 85.9% | 73.3% | 10.4% | 2.4% |
| Neutral protease-digested peptide | 90.2% | 77.9% | 21.0% | 14.1% |
| Papain-digested peptide | 86.7% | 72.3% | 15.4% | 1.1% |
| Pepsin-digested peptide | 78.3% | 68.4% | 13.4% | 3.6% |
| Neutral protease and trypsin-digested peptide | 91.9% | 19.2% | 23.3% | 8.3% |

TABLE 3-continued

Results of the determination of the antioxidant
effect of each protein peptide of broccoli

| Scavenging rate | concentration | | | |
|---|---|---|---|---|
| Peptide | 100 mg/ml | 10 mg/ml | 1 mg/ml | 0.1 mg/ml |
| Soybean protein peptide | 75.6% | 26.8% | 10.2% | 6.3% |
| Reduced glutathione (GSH) | 95.9% | 90.9% | 72.1% | 30.8% |

It can be seen from table 3 that the DPPH free radical scavenging rates of the neutral protease-digested peptide, neutral protease and trypsin-digested peptide were significantly better than that of other single enzyme-digested peptides, and can reach 10% of that of reduced glutathione (the reducing power is about 10 mass % of GSH), the rate is significantly better than soybean protein peptide.

Example 5

Investigation of the influence of protease-digested peptides obtained in examples 2 and 3 on blood lipid levels of golden hamsters with hypercholesterolemia.

(1) Materials of the Experiment (1.1) Animals

Golden hamster, male, 120, weight of 70-90 g, provided by Beijing Wei Tong Li Hua Experimental Animal Technology Co., Ltd., certificate number: SCXK (Beijing) 2006-0009.

Animals were fed in the animal houses of the pharmacological center of the Central Research Institute of Zhejiang Hisun Pharmaceutical Co., Ltd., room temperature: 20-28° C., humidity: 40-70%, ventilation times: 8-10 times per hour. The feed to the hamster was the standard feed (mice feed) provided by the experimental animal center in Zhejiang Province, the executive standard was GB14924-2001. The high fat diet was homemade (formula: 0.3% cholesterol, 20% palm oil, 79.7% basal feed).

(1.2) Drugs and Reagents

Drugs tested: The alkaline protease and neutral protease compound enzyme-digested peptide obtained in example 2, the neutral protease-digested peptide, the bromelain-digested peptide, the papain-digested peptide, the pepsin-digested peptide, the trypsin-digested peptides, alkaline protease-digested peptide obtained in example 3.

The above drugs were stored at 4° C. to 8° C. and formulated with 1% CMC (sodium carboxymethylcellulose CMC-Na) to the required concentration.

Reagents and Kits:

Ether: analytical grade, Hangzhou Chemical Reagent Co., Ltd., batch number: 20131112;

Total cholesterol (TC), batch number: 20140725;

Low density lipoprotein (LDL-C), provided by Shanghai Kehua. Bioengineering Co., Ltd.

(1.3) Instrument

Xi Sen Mei Kang automatic biochemical analyzer, model CHEX-180.

(2.) Experimental Methods and Results (2.1) Method

With the reference to the regulations and literatures such as State Food and Drug Administration Order No. 28, "Drug Registration Management Measures" (Secretary: Shao Mingli issued, Oct. 1, 2007) and New Drugs (Western medicine) Preclinical Research Guidelines (Pharmacy Pharmacology Toxicology), the hamsters were allowed to acclimate for 7 days, they can drink and eat freely, light period of 10 h/14 h, on the 8th day, animals were fed with high fat feed and were fed for 3 weeks, then the animal were anesthetized with ether, weighed, then 0.5 mL blood were obtained from postorbital vein, 0.5% heparin was used for anticoagulation, centrifuged at 5000 rpm for 10 minutes, the plasma was absorbed. The levels of TC and LDL-C in the plasma were measured by automatic biochemical analyzer, and the animals were grouped based on their blood lipid level and weight, the grouping are as shown in the following table:

TABLE 4

Grouping situation.

| Group | Dose (g · kg$^{-1}$) | Number of animals | Administration route | Volume of administration |
|---|---|---|---|---|
| Model | — | 8 | ig (gavage) | 10 ml/kg |
| Neutral protease-digested peptide | 0.5 | 8 | ig (gavage) | 10 ml/kg |
| Alkaline protease and neutral protease compound enzyme digested peptide | 0.5 | 8 | ig (gavage) | 10 ml/kg |
| Bromelain-digested peptide | 0.5 | 8 | ig (gavage) | 10 ml/kg |
| Papain-digested peptide | 0.5 | 8 | ig (gavage) | 10 ml/kg |
| Pepsin-digested peptide | 0.5 | 8 | ig (gavage) | 10 ml/kg |
| Trypsin-digested peptide | 0.5 | 8 | ig (gavage) | 10 ml/kg |
| Alkaline protease-digested peptide | 0.5 | 8 | ig (gavage) | 10 ml/kg |

The hamsters in the model group were given equal volume of menstruum. During the administration period, the hamsters in the administration group and the model group were fed with high fat feed continuously. After 10 days of administration, the animals were anesthetized with ether, weighed, then 0.5 mL blood were obtained from postorbital vein, heparin was used for anticoagulation, centrifuged at 5000 rpm for 10 minutes, the plasma was absorbed. The levels of TC and LDL-C in the plasma were measured by automatic biochemical analyzer.

(2.2) Data Processing:

The results of all the experiments were expressed with, $\bar{x} \pm s$, the comparison between any two groups used t-test. P<0.05 was statistically significant.

(2.3) Results

As shown in table 5, compared with the model group, the neutral protease-digested peptide, the papain-digested peptide can both significantly reduce the TC (*P<0.05, **P<0.01); the papain-digested peptide can significantly reduce the LDL-C (*P<0.05, **P<0.01).

TABLE 5

Effect of each protein peptide of broccoli on lipid levels in hypercholesterolemia model golden hamsters after oral administration ($\bar{x} \pm s$, n = 8)

| Group | Dose (g · kg$^{-1}$) | TC | LDL-C |
|---|---|---|---|
| Model group | — | 10.54 ± 1.21 | 2.93 ± 0.75 |
| Neutral protease-digested peptide group | 0.5 | 8.79 ± 1.46** | 2.40 ± 0.52 |

TABLE 5-continued

Effect of each protein peptide of broccoli on lipid
levels in hypercholesterolemia model golden hamsters
after oral administration ($\bar{x} \pm s$, n = 8)

| Group | Dose (g·kg$^{-1}$) | TC | LDL-C |
|---|---|---|---|
| Alkaline protease and neutral protease compound enzyme digested peptide group | 0.5 | 9.60 ± 1.18 | 2.33 ± 0.33* |
| Bromelam-digested peptide group | 0.5 | 10.06 ± 1.75 | 3.05 ± 0.93 |
| Papain-digested peptide group | 0.5 | 8.83 ± 1.42** | 2.20 ± 0.41** |
| Pepsin-digested peptide group | 0.5 | 10.46 ± 1.54 | 3.01 ± 0.68 |
| Trypsin-digested peptide group | 0.5 | 11.97 ± 1.81 | 3.78 ± 0.70 |
| Alkaline protease-digested peptide group | 0.5 | 10.37 ± 1.37 | 2.73 ± 0.32 |

Compared with the model group,
*P < 0.05,
**P < 0.01.

The invention claimed is:

1. A method for preparing a broccoli protein peptide mixture, the method comprising:
   (a) adding water, anhydrous sodium sulfite, and EDTA to a raw material of broccoli protein thereby making a predigestion mixture,
   wherein the weight of the water is 4 to 8 times that of raw material of broccoli protein, the EDTA has a mass/volume ratio of 0.02-0.05 g/L, and the anhydrous sodium sulfite has a mass/volume ratio of 0.05-0.1 g/L;
   (b) digesting the predigestion mixture for 3-4 hours at a temperature with an enzyme selected from the group consisting of neutral protease, papain, alkaline protease, trypsin, pepsin, bromelain and any combination thereof, thereby forming a digested mixture;
   (c) terminating the digestion by heating the digested mixture to from 80-90° C. for from 5-15 minutes;
   (d) optionally, centrifuging or filtering the mixture from (c);
   (e) filtering the liquid from (c) or (d) with a membrane having a pore size of 100 to 500 nm;
   (f) optionally, debittering the mixture from (e) by treating with active carbon or clay; and
   (g) concentrating and/or drying the mixture from (e) or (f), thereby obtaining the broccoli protein peptide mixture.

2. The method of claim 1, wherein the enzyme is selected from trypsin and neutral protease, or alkaline protease and papain, or alkaline protease and neutral protease.

3. The method of claim 1, wherein the enzyme is neutral protease, 200-600 units of enzyme are added per gram of raw material of broccoli protein, the temperature is 50±1° C., and the pH of the digested mixture is adjusted to from 6.0-7.0 with NaOH before terminating.

4. The method of claim 1, wherein the enzyme is papain, 1000-3000 units of enzyme are added per gram of raw material of broccoli protein, the temperature is 50±1° C., and the pH of the digested mixture is adjusted to from 6.5-7.0 with NaOH before terminating.

5. The method of claim 1, wherein the enzyme is alkaline protease, 200-600 units of enzyme are added per gram of raw material of broccoli protein, the temperature is 50±1° C., and the pH of the digested mixture is adjusted to from 9.0-9.5 with NaOH before terminating.

6. The method of claim 1, wherein the enzyme is trypsin, 5-15 units of enzyme are added per gram of raw material of broccoli protein, the temperature is 50±1° C., and the pH of the digested mixture is adjusted to from 8.0-8.5 with NaOH before terminating.

7. The method of claim 1, wherein the enzyme is pepsin, 5-15 units of enzyme are added per gram of raw material of broccoli protein, the temperature is 36-38° C., and the pH of the digested mixture is adjusted to from 1.5-2.5 with NaOH before terminating.

8. The method of claim 1, wherein the enzyme is bromelain, 1000-5000 units of enzyme are added per gram of raw material of broccoli protein, the temperature is 40±1° C., and the pH of the digested mixture is adjusted to from 6.0-7.0 with NaOH before terminating.

9. The method of claim 1, wherein the enzyme is a combination of at least 2 proteases, 5-3600 units of enzyme are added per gram of raw material of broccoli protein, the temperature is 50±1° C., and the pH of the digestion is controlled to 8.0-8.5 for the initial 0.5-1 hour and then not controlled for the remainder of the digestion.

10. The method of claim 9, wherein the combination of at least 2 proteases is selected from trypsin and neutral protease, or alkaline protease and papain, or alkaline protease and neutral protease.

* * * * *